US011583435B2

(12) United States Patent
Mikkonen et al.

(10) Patent No.: US 11,583,435 B2
(45) Date of Patent: Feb. 21, 2023

(54) ARRANGEMENT FOR AN INTRAUTERINE SYSTEM AND ITS INSERTER

(71) Applicant: Bayer OY, Turku (FI)

(72) Inventors: Joonas Mikkonen, Lempäälä (FI); Tero Jalkanen, Turku (FI); Mikko Virtanen, Halikko (FI); Taina Tjaeder, Piispanristi (FI); Karym El Sayed, Berlin (DE)

(73) Assignee: Bayer HealthCare LLC, Whippany, NJ (US)

( * ) Notice: Subject to any disclaimer, the term of this patent is extended or adjusted under 35 U.S.C. 154(b) by 0 days.

(21) Appl. No.: 16/340,034

(22) PCT Filed: Sep. 29, 2017

(86) PCT No.: PCT/EP2017/074784
§ 371 (c)(1),
(2) Date: Apr. 5, 2019

(87) PCT Pub. No.: WO2018/065310
PCT Pub. Date: Apr. 12, 2018

(65) Prior Publication Data
US 2020/0038232 A1 Feb. 6, 2020

Related U.S. Application Data

(60) Provisional application No. 62/404,822, filed on Oct. 6, 2016.

(51) Int. Cl.
A61F 6/00 (2006.01)
A61F 6/14 (2006.01)
A61F 6/18 (2006.01)

(52) U.S. Cl.
CPC .............. *A61F 6/005* (2013.01); *A61F 6/144* (2013.01); *A61F 6/18* (2013.01)

(58) Field of Classification Search
CPC .... A61F 6/00; A61F 6/005; A61F 6/06; A61F 6/14; A61F 6/144; A61F 6/18
USPC .................................. 206/363–370, 461–471
See application file for complete search history.

(56) References Cited

U.S. PATENT DOCUMENTS

| 4,019,633 A * | 4/1977 | Roth | ...................... B65D 5/503 206/364 |
| 4,111,302 A * | 9/1978 | Roth | ........................ A61F 6/14 206/363 |
| 4,402,407 A * | 9/1983 | Maly | ........................ A61L 2/26 206/363 |

(Continued)

FOREIGN PATENT DOCUMENTS

| CA | 2735933 A1 * | 3/2010 | ............... A61F 6/18 |
| DE | 29819558 U1 | 2/1999 | |

(Continued)

OTHER PUBLICATIONS

"International Preliminary Report on Patentability from PCT Application No. PCT/EP2017/074784", dated Apr. 9, 2020.

(Continued)

*Primary Examiner* — Bryon P Gehman

(57) ABSTRACT

The present invention relates to an arrangement comprising an intrauterine system, an inserter for the intrauterine system and a package for the inserter.

16 Claims, 13 Drawing Sheets

(56) References Cited

U.S. PATENT DOCUMENTS

| | | | | |
|---|---|---|---|---|
| 5,370,129 A | * | 12/1994 | Diaz | A61F 6/18 |
| | | | | 128/839 |
| 5,785,053 A | | 7/1998 | MacAndrew et al. | |
| 5,842,474 A | | 12/1998 | Blyskal et al. | |
| 9,668,912 B2 | * | 6/2017 | Jutila | A61F 6/18 |
| 10,028,858 B2 | * | 7/2018 | Deckman | A61F 6/18 |
| 10,149,784 B2 | * | 12/2018 | Jutila | A61F 6/18 |
| 2011/0162656 A1 | | 7/2011 | Jutila et al. | |
| 2013/0014762 A1 | | 1/2013 | Deckman et al. | |

FOREIGN PATENT DOCUMENTS

| | | | | |
|---|---|---|---|---|
| GB | 1543841 A | | 4/1979 | |
| GB | 2293324 A | * | 3/1996 | A61F 6/18 |
| WO | 2010031900 A1 | | 3/2010 | |
| WO | 2012056105 A1 | | 5/2012 | |

OTHER PUBLICATIONS

"International Search Report and Written Opinion from PCT Application No. PCT/EP2017/07484", dated Dec. 18, 2017.

\* cited by examiner

ARRANGEMENT FOR AN INTRAUTERINE SYSTEM AND ITS INSERTER

CROSS REFERENCE TO RELATED APPLICATIONS

This application is a national stage application under 35 U.S.C. § 371 of International Application No. PCT/EP2017/074784, filed internationally on Sep. 29, 2017, which claims the benefit of priority to U.S. Provisional Patent Application No. 62/404,822, filed Oct. 6, 2016.

FIELD OF THE INVENTION

The invention relates to an arrangement comprising an intrauterine system, its inserter and its package. The invention also relates to a package for an inserter for an intrauterine system.

BACKGROUND OF THE INVENTION

Various types of inserters have been developed for the positioning of mechanical and copper wire-containing intrauterine devices (IUDs) as well as of intrauterine systems having a drug containing cylinder (IUSs). In the following, IUD and IUS can be used interchangeably and when one is mentioned, it is to be understood that either of them can be used. Simple rod-shaped inserters have been suggested for inserting relatively small or sufficiently flexible intrauterine devices in their original, expanded shape by using simple push-in technique. However, most common inserters are constructed for introducing the device into the uterus in a contracted state. These inserters usually comprise an insertion tube having a relatively narrow diameter and a rounded, blunt end which will pass through the cervical canal easily and will not damage or injure the fundus upon contact therewith, and a plunger inside the insertion tube. Prior to insertion the device, whether an IUD or an IUS, is usually retracted into the insertion tube either by means of string(s) attached to the device and intended for the removal of the device from the uterus, or by pushing the device into the insertion tube by a plunger with inserters having a special window to adapt the device in the expanded shape. Then the insertion tube with the device therein is introduced through the cervical canal into the uterus. When the device is correctly positioned, it is released either by pushing the plunger towards the uterus or by holding the plunger steady and by retracting the insertion tube outwards. Once expulsed from the insertion tube within the uterine cavity, the device is supposed to resume its original expanded shape.

A typical example of an intrauterine device has a T-shaped body fabricated of plastic material and consisting of an elongated body part having at one end a transverse member comprising two wings, the elongate member and the transverse member forming a substantially T-shaped piece when the device is in the expanded configuration, for example positioned in the uterus. The tips of these wings are preferably hemispherical in order to facilitate the introduction of the device through the cervical canal. The elongate member has a copper spiral or wire or a hormone capsule arranged around the body. The end of the vertical body part has a loop with a string or strings attached to it, with which the device can be removed from the uterus after use or whenever needed.

Challenging steps, which will be exemplified with a common T-shaped device, apply as well to intrauterine systems having another type of frame, for example 7-shaped or closed, continuous frames.

For the insertion of a T-shaped intrauterine system it is extremely important that the hemispherical ends of the transverse member are in the exactly correct position in relation to the edge of the insertion tube at the moment of introducing the device in the uterus. If the IUS is pulled into the insertion tube by means of the removal string, which is usually the case with the existing devices, it is understandable that it is difficult to make the IUS stop in the correct position, especially if the relative movement of the insertion tube and the plunger is not restricted by any stop member. Pulling with too much force easily makes these ends enter almost completely into the insertion tube. During the insertion of the device, the sharp edges of the insertion tube may interfere with the introduction of the device through the cervical canal. On the other hand, if the device is not drawn deep enough into the insertion tube, the frame ends project outwardly because of a relatively wide insertion tube. The diameter at the level of the wings remains too wide, which makes the introduction of the device more difficult. When the device is pulled into the insertion tube, it is important that the device is in the correct position, i.e. without damaging the loop, the rest of the body or the string(s). If the device is pulled inside the insertion tube in a wrong position, the edges of the insertion tube can damage the loop or the body. If pulling is continued and the device does not turn into the correct position, the string(s) will finally cut through the loop or the body, which can also cause the device to get jammed within the insertion tube.

Some known inserters are such that the IUS is in fact not pulled inside the insertion tube, but rather the insertion tube is moved towards the proximal end of the inserter, to cover the whole of the IUS. Therefore, in case the inserter comprises a slider, this slider is not moved downwards (i.e. towards the user) as one would intuitively expect, but rather moved upwards (i.e. away from the user). If with such an inserter, the slider is moved initially to the wrong direction (towards the user), the IUS is prematurely released and is thus unusable. Indeed, it is not recommended to re-assemble the device, for obvious hygienic reasons. One of the aims of the present inventions is thus to provide a package for an inserter with which the user cannot make this kind of mistake.

Thus, some intrauterine systems, for example those with a T-shaped body, cannot be inserted inside a patient's uterus in their unfolded state, but also cannot be stored inside an inserter for a long period of time, in a ready-for-insertion state with the horizontal arms also inside the tube. Indeed, should such an intrauterine system be stored for an extended period of time, it might not properly retrieve its original and intended shape due to a memory effect of the material used of the body, thus not fitting properly inside the uterus. Therefore, this kind of intrauterine systems are typically stored in their sales package in a manner that any straight part of the intrauterine system is stored inside the inserter and the remaining part of the intrauterine system is withdrawn inside the inserter by the physician, immediately prior to the insertion. This step can be seen as cumbersome and can lead to the intrauterine system being not entirely correctly positioned inside the insertion tube (either not enough or too much). This could have an effect on the asepticity of the implant. There exists thus a need to provide a package for an intrauterine system and its inserter that would overcome this problem. An aim is thus also to increase patient security and easiness of use for the physician. Another aim is to provide an arrangement where the steps required to be performed by the physician are reduced.

SUMMARY OF THE INVENTION

The present description relates to an arrangement comprising an intrauterine system, an inserter for the intrauterine system and a package for the inserter, wherein the inserter comprises a handle having a first end and a second end, an insertion tube having a first end and a second end, first handling means for withdrawing the intrauterine system inside the insertion tube and second handling means for expulsing the intrauterine system from the insertion tube, and the package comprises a container, a cover arranged to close the container and means for actioning the first handling means of the inserter.

The present description also relates to a package for an inserter for an intrauterine system. In some embodiments, the package comprises a container, a cover arranged to close the container and means for actioning a first handling means of the inserter for withdrawing the intrauterine system inside an insertion tube of the inserter, when then inserter is removed from the package.

BRIEF DESCRIPTION OF THE DRAWINGS

The invention will now be described, by way of example only, with reference to the accompanying drawings, in which.

DETAILED DESCRIPTION

Figure 1:
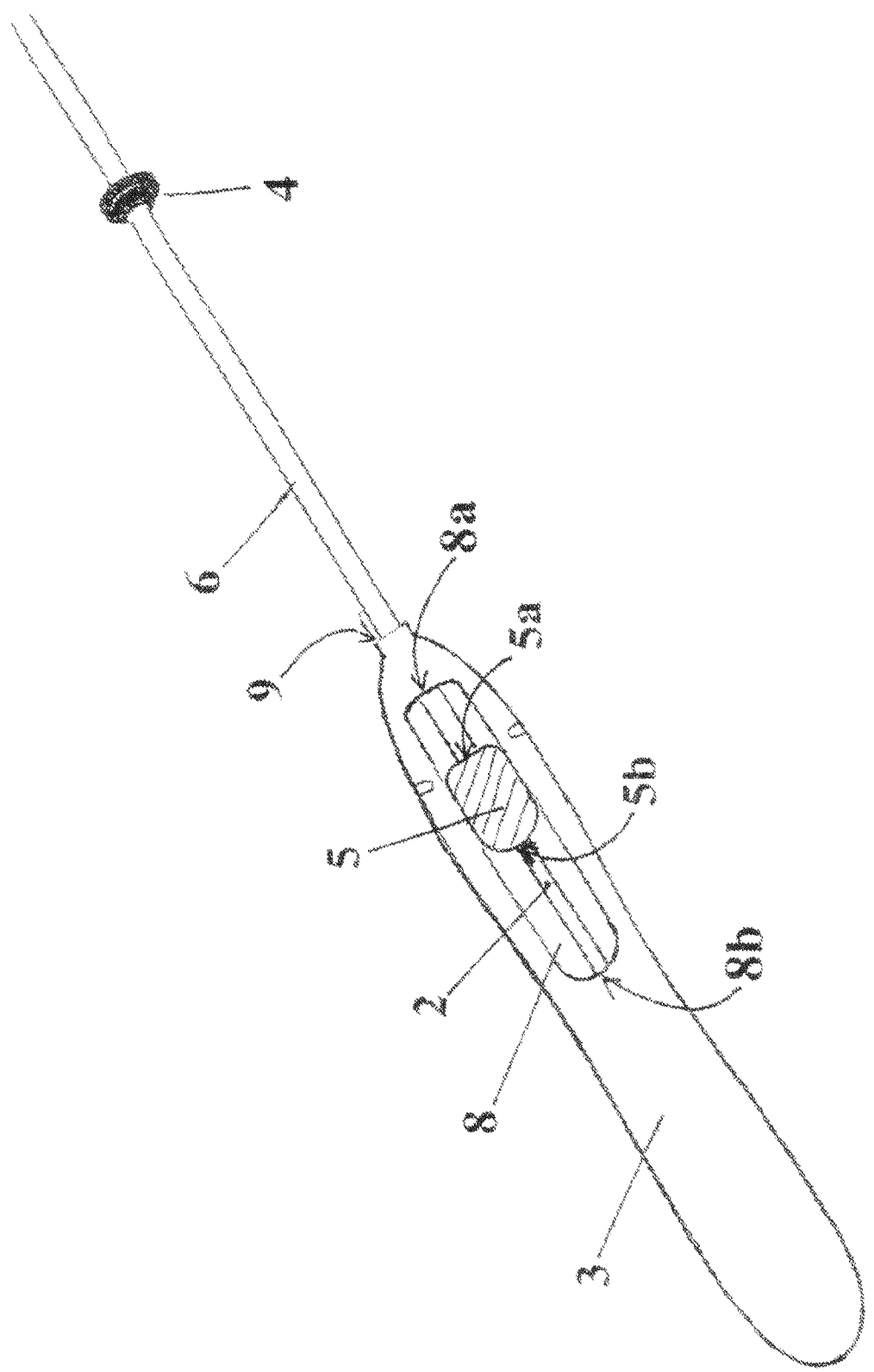
FIG. 1 schematically illustrates an inserter according to an embodiment.

The present description relates to an arrangement comprising an intrauterine system, an inserter for the intrauterine system and a package for the inserter, wherein the inserter comprises a handle having a first end and a second end, an insertion tube having a first end and a second end, first handling means for withdrawing the intrauterine system inside the insertion tube and second handling means for expulsing the intrauterine system from the insertion tube, and the package comprises a container, a cover arranged to close the container and means for actioning the first handling means of the inserter.

The present description thus presents an arrangement, wherein the intrauterine system is automatically loaded inside the inserter when it is removed from the package. This effect is obtained by a suitably designed package, depending on the structure of the inserter used. The package has a structure that keeps the handle in place but allows it to be easily removed by grabbing it with a hand.

In the present description and claims, by first ends are typically meant the ends that are closer to the uterus during the insertion of the intrauterine system, also called forward ends. Second ends are the ends opposite to the first ends, also called distal ends. The term removal string means one or more strings used for removing the system once it reaches the end of its use time. There may thus be one or more such strings, and this term encompasses also strings that are not used for removal but only for locking the device during insertion.

In some embodiments, the means for actioning the first handling means of the inserter comprises a form capable of exerting a force of 10-30 N to the inserter when the inserter is pulled away from the container. Indeed, the force the package exerts on the inserter shall be large enough for the IUS to be pulled inside the inserter, but small enough to avoid breaking the inserter. In some embodiments, the force required should also be such that a user, when removing the inserter from the package, first needs to exercise only a relative low force for the loading of the IUD, and then a slightly larger force to remove the inserter from the package, without breaking the inserter. The package may also comprise means that release the means for actioning the first handling means, once the IUS is correctly positioned inside the inserter. One example is given below in connection with a specific example of the inserter.

The force required to be exerted on the inserter can be from 10, 11, 12, 13, 14, 15, 16, 17, 18, 19, 20, 21, 22, 23, 24, 25, 26, 27, 28 or 29 N up to 11, 12, 13, 14, 15, 16, 17, 18, 19, 20, 21, 22, 23, 24, 25, 26, 27, 28, 29 or 30 N. The force required may also be higher, depending on the structure and strength of the inserter. The required force naturally needs to be low enough so as to not cause any breaking of the inserter.

In some embodiments, the means for actioning the first handling means of the inserter is a locking throttle arranged in connection with the container of the package. The locking throttle may comprise two parts that rotate with respect to each other. For example, the locking throttle may be arranged in a first, open position when the inserter is packaged and turned to a second, closed position for storage. Such an arrangement would make the packaging operation easier. The force exerted on the inserter when it is being removed from the package then creates a frictional force that is high enough for the IUS to be loaded inside the insertion tube. The two parts may thus have each an opening through their thickness, and the openings may be arranged slightly off-lined (eccentric) one with respect to the other.

The locking throttle may also be made of two halves between which the insertion tube is arranged during the packaging. In some embodiments, the halves are then attached to each other, for example by gluing, with ultrasound welding or by snap locking parts. Again, such locking throttle would make the packaging easier. In case such a locking throttle is used, it has a tight enough grip on the insertion tube, that it forces the insertion tube to move towards the proximal end of the inserter, thus actioning the first handling means of the inserter (for withdrawing the intrauterine system inside the insertion tube) in an indirect manner.

In some embodiments, the inserter is as follows:
the handle of the inserter has a longitudinal opening at its first end, said opening having a longitudinal axis parallel to the longitudinal axis of the inserter, the first handling means comprises
- a movable slider arranged in said longitudinal opening and having a first end and a second end, and
- locking means for reversibly locking the intrauterine system in relation to the plunger,
- the second handling means is a plunger having a first end and a second end, attached by its second end to the slider,
- the insertion tube is arranged around the plunger, and
- the inserter further comprises locking means for reversibly locking the intrauterine system in relation to the plunger via a removal string of the intrauterine system.

This type of inserter is discussed in more detail below. In some embodiments, said locking means is controllable by the slider and/or by the insertion tube.

In some embodiments, the cover is arranged to open only partially. The cover may for example comprise a perforated line where the opened part of the cover breaks away from the rest. The cover may also be made of two different materials, wherein the openable part is detached from the rest of the cover when the package is opened.

In some embodiments, the container is made of a plastic material. The cover may also be made of a plastic material. Furthermore, either or both of the container and cover may be made of a fibre reinforced plastic material. Indeed, the material of the container and/or the cover can be for example polyethylene, polypropylene, polyester, polyamide or the like. The reinforcing fibres may be for example plastic fibres or glass fibres. Especially the cover may be made also from a nonwoven material, such as spunbond nonwoven materials or flashspun nonwoven materials. Once such suitable material is sold under the tradename Tyvek®.

The container, when made of plastic material, may be manufactured in any suitable manner. For example, it may be thermoformed from a sheet of material, or it may be made by injection moulding. The container may also comprise several parts. For example, it may consist of a cardboard box and a separate part called primary package on which the inserter is arranged, that is made of a plastic material. This primary package is arranged inside the box. In case no added box is used, the discussion below concerning the primary package applies to the container. The cover may be arranged to close both the box and the primary package, or both the primary package and the box may have their own covers.

The primary package may thus be formed such that the means for actioning the first handling means of the inserter is an integral part of the primary package or the primary package may comprise a separate means for actioning the first handling means, as an insert to be arranged on the primary package or the container. The means for actioning the first handling means can also be arranged around the insertion tube or around the flange, is a flange is used. For the latter option, the flange needs to be designed such that it is fixed on the insertion tube and needs to be compressed in order to be able to move it.

One type of inserter especially suitable for use in the present arrangement is as described in WO 2010/031900, the contents of which are hereby incorporated by reference.

Indeed, one inserter that is particularly suitable for the present description comprises a handle, a plunger (second handling means) attached to the handle, a slider (first handling means), an insertion tube around the plunger, the second end of the insertion tube being attached to the slider or to the means to move the slider. The inserter also comprises means for reversibly locking the removal string(s) of the intrauterine system in such a way that the IUS remains immobile in relation to the plunger during the necessary steps prior to and during insertion, and again for releasing the string(s) and the IUS after it has been inserted. The inserter further comprises an opening in a part of the handle and a channel in which the insertion tube slides in the longitudinal direction, Additionally, the insertion tube may comprise a flange, which can be adjusted so that its distance from the first end of the insertion tube corresponds to the depth of the uterus.

The part of the handle that is closer to its first end has an opening having a first end and a second end, which opening runs in the direction of the plunger. The surface of the first end of the slider and the surface at the first end of the opening together form a first pair of stop members, and the surface of the second end of the slider and the surface at the second end of the opening together form a second pair of stop members. When inserting the IUS, the slider and the insertion tube can be moved forward until the surfaces and contact each other, and backwards until the surfaces and contact each other. The locking means are arranged inside the handle.

In some embodiments, the longitudinal opening on the handle can be also quite narrow and does not need to be symmetrically positioned on the handle and with respect to the longitudinal axis. This type of inserter is especially suitable for use with the present package, as the automatic loading prevents the IUD from being accidentally released before insertion, Indeed, as the loading of the IUD inside the inserter is done by pushing the slider forwards, it may be seen as unintuitive by some physicians.

This type of inserter may be used as follows. In the package, the IUS is placed in the first end (i.e. the front end, i.e. the end of entry into the uterus) of the inserter so that the elongate member of the device with a drug containing reservoir is inside the insertion tube with the tip of the elongate member abutting the end of the plunger. The means to move the slider is on a starting or initial position, and the removal string(s) inside the inserter are tightened and locked by the locking means.

In some embodiments, the package is opened by pulling on the cover closing the container of the package. The cover may open partially or fully and the shape of the package is such that the handle can be easily grabbed and the inserter drawn out of the package. The drawing out-gesture may be a direct pulling or it may require slightly lifting and pulling the inserter with respect to the package. The means for actioning the first handling means of the inserter thus enter into action and pull the slider towards the first end of the insertion tube. The slider is moved towards the first end of the insertion tube until the forward surface of the slider abuts the forward surface of the opening of the handle (at the first end of the opening), thereby stopping the movement of the insertion tube. At this moment the IUS is substantially inside the insertion tube, and ready for insertion.

In some embodiments, distance the slider and the insertion tube move between these surfaces has been designed substantially to correspond to the length of the IUS assembled for insertion. The first end of the insertion tube is stopped at a level at which the hemispherical tips of the wings of the IUS partly remain uncovered by the insertion tube, while the wings still remain together.

In some embodiments, the force required to withdraw the inserter from the package is thus larger than the force required to move the slider towards the first end of the insertion tube but smaller than the force that would be needed to break the inserter apart (i.e. for example that the insertion tube would detach from the handle). Thus when the forward surface of the slider has abutted the forward surface of the opening of the handle, the inserter can be removed from the package.

In some embodiments, the inserter in this configuration is introduced into the uterus until the IUS is in the correct location (this can be for example be shown with the help of the flange as mentioned above), where after the device is released from the insertion tube. While retaining the inserter stationary, the insertion tube is retracted towards the handle by moving the slider backwards until the distal surface of the slider abuts the distal surface of the opening (at its second end) of the handle. In some embodiments, the distance the slider and the insertion tube can be moved has been selected to indicate clearly the moment at which the IUS has completely been released from the insertion tube moving towards the handle.

In some embodiments, the package and especially its container may also comprise a specific means for releasing the means for actioning the first handling means of the inserter. For example, when the slider reaches the position where it abuts to the forward end of the opening, this could mechanically open the means for actioning, thus releasing the inserter.

In some embodiments, the means for actioning the first handling means can comprise for example a throttle that forces the IUS swings to close and a separate part that keeps the throttle on its place in the package. This may be useful if the package is made of thermoformed plastic sheet.

The handle can have many shapes and is preferably designed for easy handling of the inserter even by using only one hand. In some embodiments, the plunger attached to the handle is advantageously hollow or has a groove or bore running in the axial direction thus allowing the string(s) to slide freely in it, without any risk of them getting jammed between the plunger and the insertion tube. The first end, i.e. the forward end of the plunger is preferably suitably shaped to have for example a notch, an indentation, an eyelet, a funnel or a groove to adapt to the lower end of the intrauterine system and to enable the optimal and secure positioning of the intrauterine system on the plunger so that the probability of damage to the intrauterine system is minimal. Thus the IUS will not be twisted when it is drawn in the insertion tube or during insertion and assumes a specified constant configuration when released.

In some embodiments, the slider mechanism is preferably inside the handle and comprises at least one elongated element, which can be moved in the longitudinal direction of the plunger. In some embodiments, the slider comprises means to move the slider, which preferably is a part of the slider, and the insertion tube attached to said means. In some embodiments, the slider comprises at least two elements, preferably parallel, which are combined on at least one point by a transversal member. In some embodiments, the transversal member may form means, for example a knob or switch, by which the slider can be moved. The handle can comprise one or more means to connect the slider elements and to facilitate the movement of the slider, for example a support, a shoulder, a holder, a saddle, a groove or a slot. In some embodiments, the slider preferably comprises at least one structural element, for example an extension, which is capable to generate the necessary operation of the locking means to keep the strings immobilized during storage or during preparatory steps before insertion or during insertion and/or to release the string(s) when the slider is moved to the backward position. In the following description, the term slider is used to designate both the slider itself and the means to move the slider attached to the slider. The term slider is thus used for convenience of reading.

The locking means is any arrangement which, induced by the movement of the slider or of the means to move the slider and the insertion tube, can immobilise the removal string(s) to hold the IUS in a stable position and/or to release the string(s) after insertion to release the IUS. The locking means can be for example according to what has been described in WO 2010/031900. Particularly, the locking means comprises an object capable of reversibly preventing and/or allowing the movement of the string(s) by at least partly moving or pivoting from the original position, for example rotating around a shaft or an axle, and vertically or horizontally attached to the handle. The object may have several shapes and may be for example round or rod-shaped, wedge, polygonal or rectangular with rounded or sharp corners. The surface of the object preferably comprises one or more extensions having variable size and shape, for example a knob, a rib or a switch. When the slider mechanism is moving backwards, at a suitable point a part or an extension of the slider or of the insertion tube is pressed against at least one extension of the object thus changing its orientation enough relative to the original position to cause release of the string(s). Preferably the object has a slot or pinhole through which the string(s) run. The locking means may also comprise at least one counterpart against which the string(s) are pressed by the object and thus reversibly immobilized in the locking position. In some embodiments, the counterpart has a suitable shape adapted to fit at least some part of the surface of the object. An extension, or extensions of the object can be used to keep the object and the counterpart in a fixed configuration until the slider is moved backwards to release the IUS. The counterpart preferably has a suitable design to keep the string(s) in proper direction, for example a slot or pinhole through which the string(s) run. Further, the object and said at least one counterpart have preferably a suitable length and diameter to fit inside the handle.

The intrauterine system used in the present arrangement can be any device or system known in the art. Moreover, any inserter where the intrauterine system cannot be stored for an extensive period of time, can be used in connection with the present arrangement. Indeed, the package is suitable for any type of inserter.

According to an embodiment, the intrauterine system comprises a T-shaped body and an elastomeric capsule containing a therapeutically active agent. According to another embodiment, the intrauterine system comprises a triangular shaped body and at least one capsule containing a therapeutically active agent. The intrauterine systems may also comprise more than one capsule, and each capsule may comprise a different therapeutically active agent. One capsule may also comprise more than on therapeutically active agent. The therapeutically active agents are any agents known and useful as such, for example contraceptives or agents benefiting from a local release in the uterus.

The present description also relates to a package for an inserter for an intrauterine system. In some embodiments, the package comprises a container, a cover arranged to close the container and means for actioning a first handling means of the inserter for withdrawing the intrauterine system inside an insertion tube of the inserter, when then inserter is removed from the package. The inserter is thus as described above, and the means for actioning the first handling means of the inserter comprises a form capable of exerting a force of 10-30 N to the inserter when the inserter is pulled away from the container.

The present description also relates to a method for positioning an intrauterine system in a uterus of a patient, wherein the method uses an arrangement according to the present description. The method comprises the steps of
opening the cover of the package,
slightly lifting the handle of the inserter, in order to be able to correctly grab the handle,
pulling the inserter out of the package, during which pulling the intrauterine system is automatically loaded inside the insertion tube,
introducing the inserter into the uterus of the patient until the intrauterine system is in its correct location,
releasing the intrauterine system from the inserter,
removing the inserter from the uterus of the patient.

The method advantageously contains, at its beginning, the further steps of sounding the uterus using a probe, and setting the flange accordingly to show the correct insertion depth.

When using the inserter as explained in more detail in this description, the IUS is released by drawing it backwards, by retracting the slider towards the handle all the way until the second pair of stop members gets together. In some embodiments, the movement of the slider also releases the locking means thus releasing the removal string(s). The distance the slider or the insertion tube moves has been selected so that at this point the IUS has completely been released from the insertion tube.

DETAILED DESCRIPTION OF THE DRAWINGS

In the following description, the term slider and the corresponding reference number are used to designate both the slider itself and the means to move the slider attached to the slider. The term slider is thus used for convenience of reading.

FIG. 1 illustrates a general overview of an inserter according to an embodiment. The inserter comprises a handle 3, a plunger 2 attached to the handle, a slider 5, an insertion tube 6 around the plunger, the second end of the insertion tube being attached to the slider or to the means to move the slider. The inserter also comprises means for reversibly locking the string(s) (not shown). The inserter further comprises an opening 8 in a part of the handle, a channel 9 in which the insertion tube slides in the longitudinal direction and a flange 4.

The handle 3 has an opening 8 having a first end 8a and a second end 8b, which opening runs in the direction of the plunger 2. The surface of the first end 5a of the slider 5 and the surface at the first end 8a of the opening 8 together form a first pair of stop members, and the surface of the second end 5b of the slider 5 and the surface at the second end 8b of the opening 8 together form a second pair of stop members. The locking means are arranged inside the handle 3 and are thus not visible.

Figure 2A:
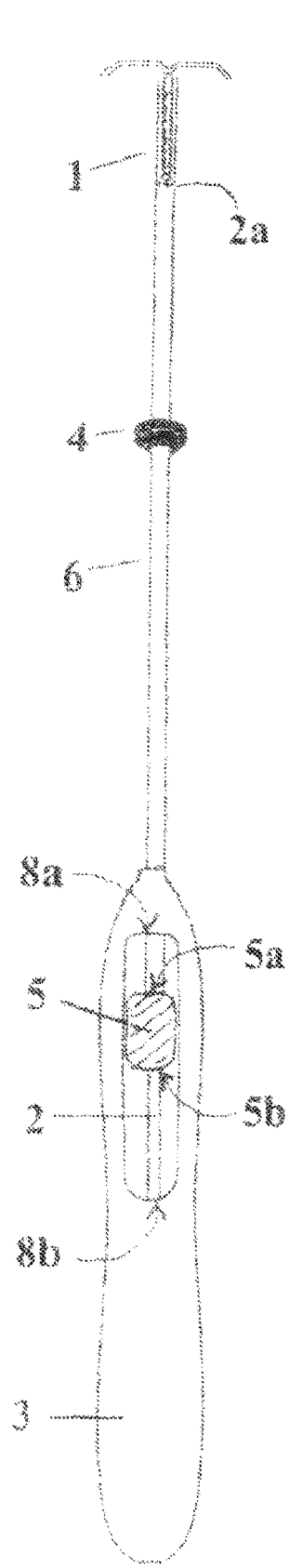
FIG. 2A-2C illustrate an operating principle of the inserter of FIG. 1.
Figure 2B:
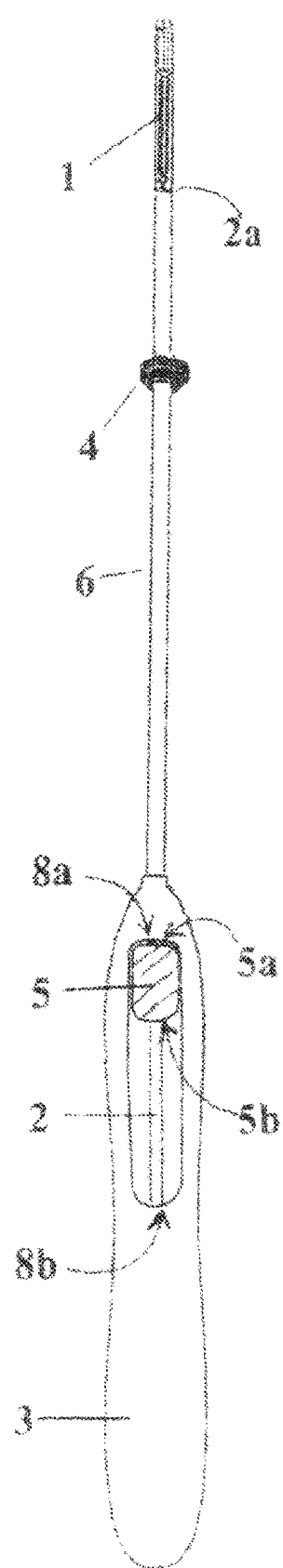
Figure 2C:
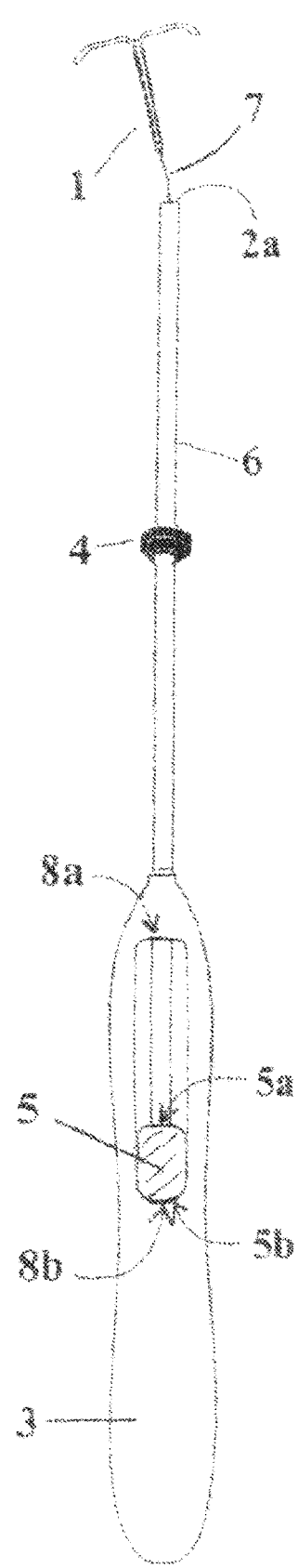

FIGS. 2A, 2B and 2C illustrate an operating principle of the inserter shown in FIG. 1.

FIG. 2A shows an inserter and a T-shaped IUS 1 in a configuration as they are in a sterilized package. The IUS is placed in the first end (i.e. the front end, i.e. the end of entry into the uterus) of the inserter so that the elongate member of the device with a drug containing reservoir is inside the insertion tube 6 with the tip of the elongate member abutting the end of the plunger (shown with reference number 2a). The means to move the slider 5 is on the starting or initial position, and the removal string(s) inside the inserter are tightened and locked by the locking means (not shown in the Figure).

FIG. 2B illustrates the first step of insertion procedure. The insertion tube is moved towards the IUS by pushing the slider forward until surface 5a abuts the surface 8a of the opening 8 of the handle 3, thereby stopping the movement of the insertion tube. This step is automatically carried out by the present package.

FIG. 2C illustrates the procedure to release the IUS. The device in the configuration according to FIG. 2B is introduced into the uterus until the IUS is in the correct location, where after the device is released from the insertion tube. While retaining the inserter stationary, the insertion tube is retracted towards the handle by moving the slider 5 backwards until the surface 5b of the slider abuts the surface 8b of the opening 8 of the handle 3.

Figure 3:
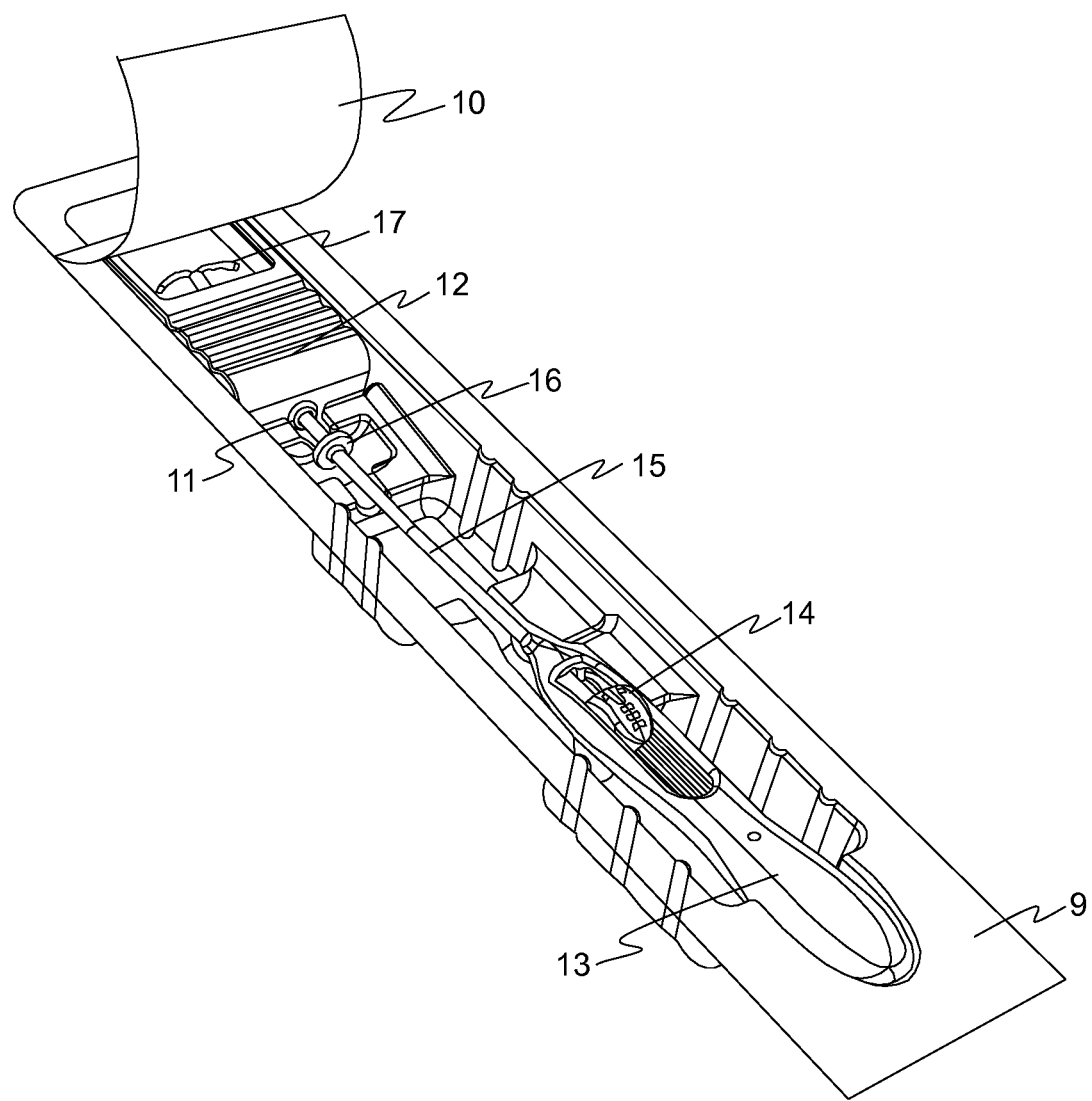
FIG. 3 illustrates an arrangement according to an embodiment.

FIG. 3 illustrates an arrangement according to an embodiment. In this Figure, an inserter is shown in its package. The package comprises a container 9, a cover 10, a locking throttle 11 and a locking part 12 for keeping the locking throttle 11 in its place. The inserter comprises a handle 13, a slider 14 (as first handling means for withdrawing the intrauterine system inside the insertion tube), insertion tube 15 and a flange 16. Part of the intrauterine system 17 is also visible below the locking part 12. The cover 10 has been partially opened and the inserter is ready to be removed from the package.

Figure 4:
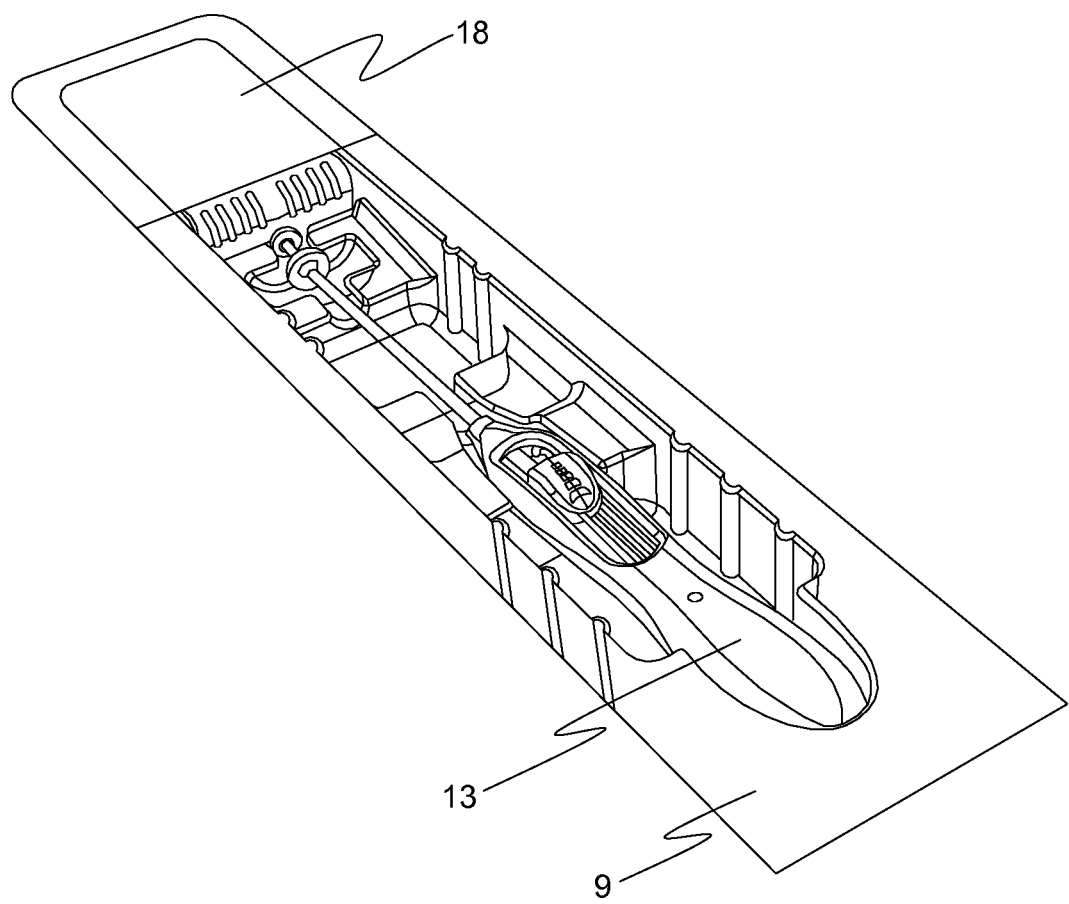
FIG. 4 illustrates an arrangement according to another embodiment.

FIG. 4 illustrates an arrangement according to another embodiment. In this embodiment, the cover 18 is in two parts, and the Figure illustrates the moment when a first part has been removed, leaving most of the inserter accessible. At this moment, the inserter can be grabbed by its handle 13 and removed from the container 9.

Figure 5A:
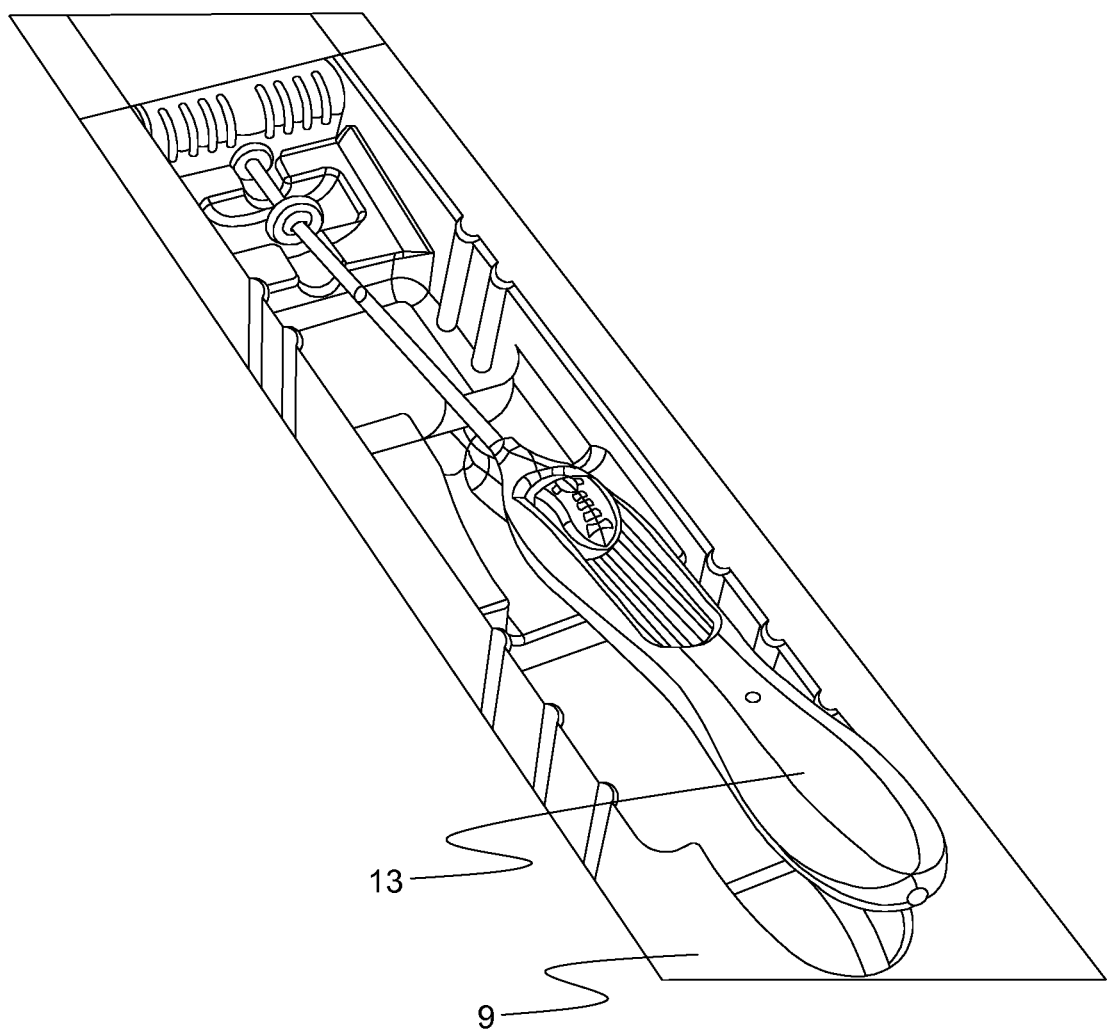
FIG. 5A-5D illustrate different steps of removing an inserter from a package as illustrated in FIG. 4.
Figure 5B:
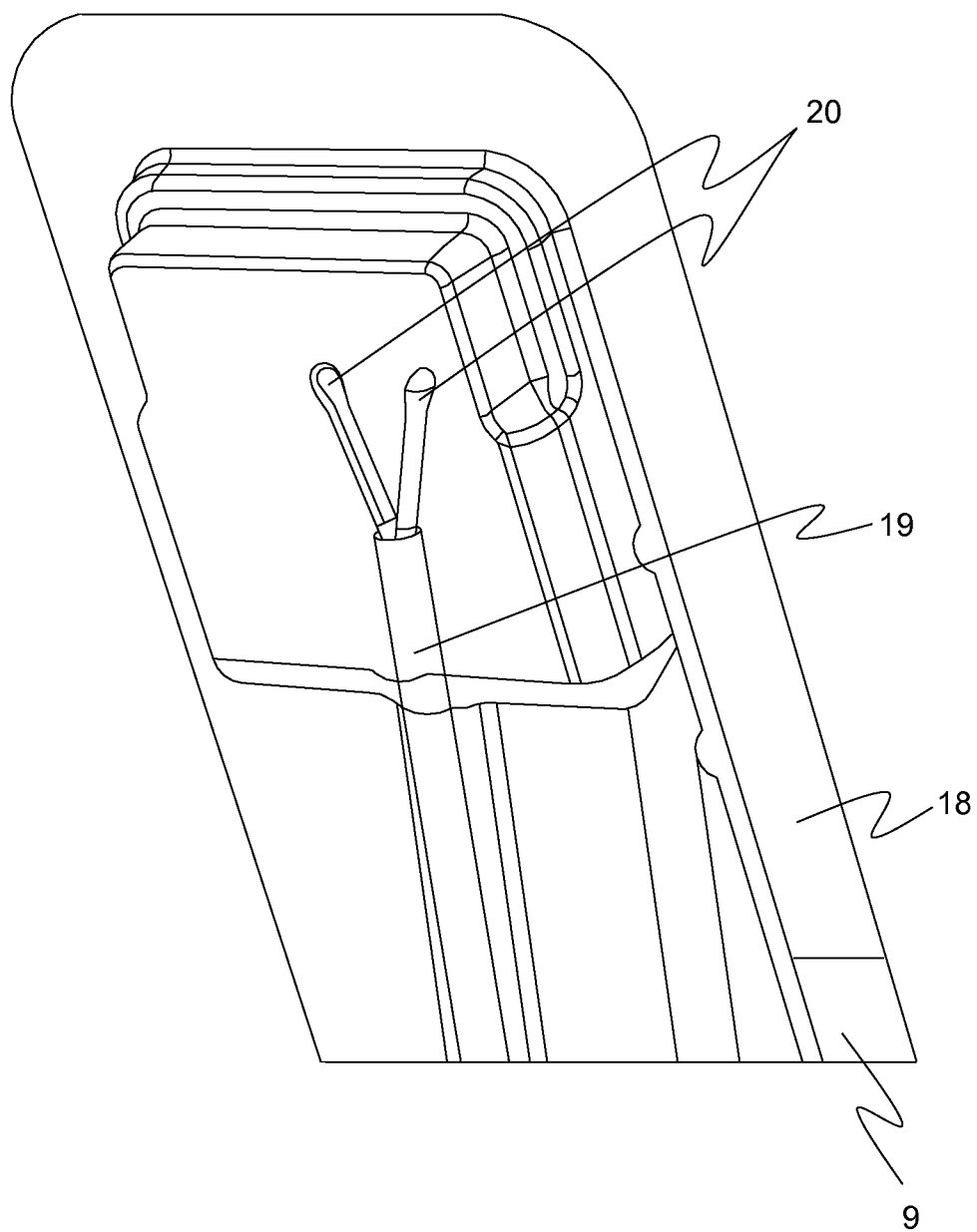
Figure 5C:
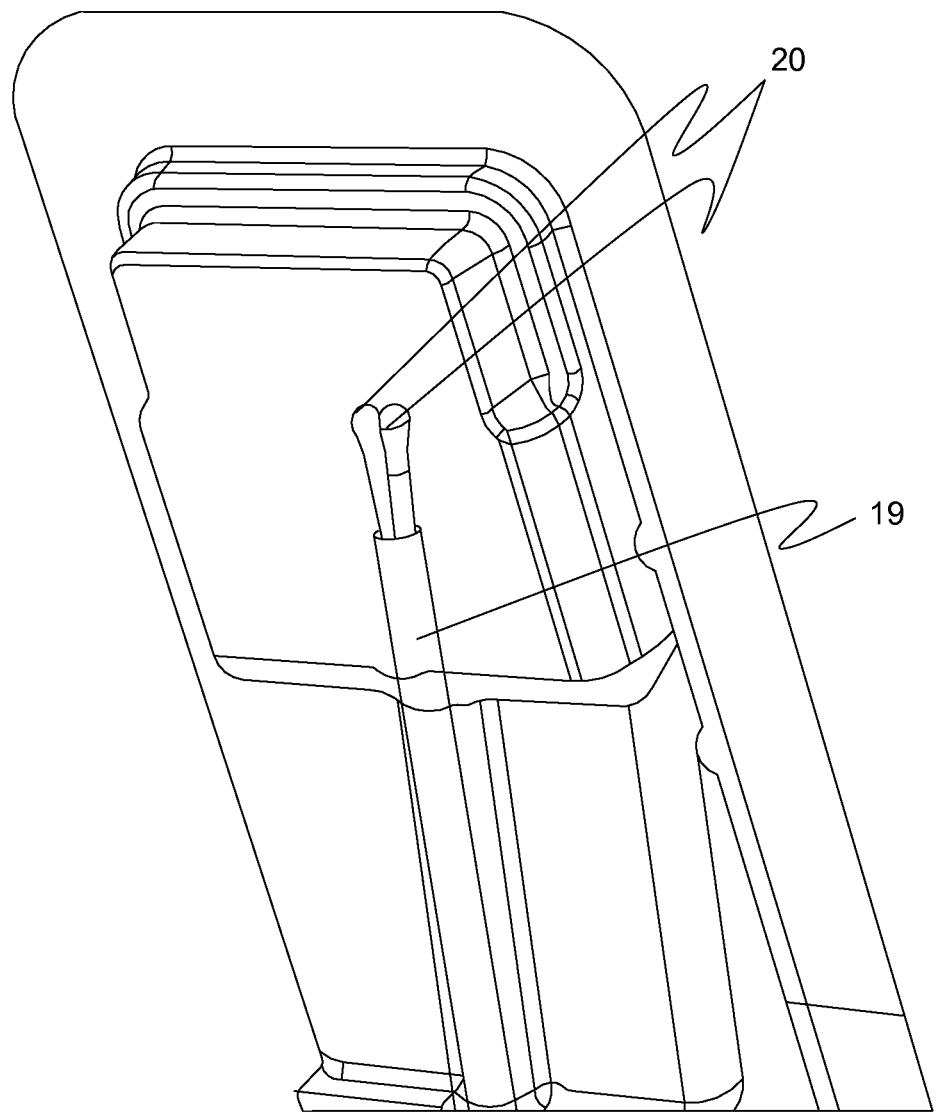
Figure 5D:
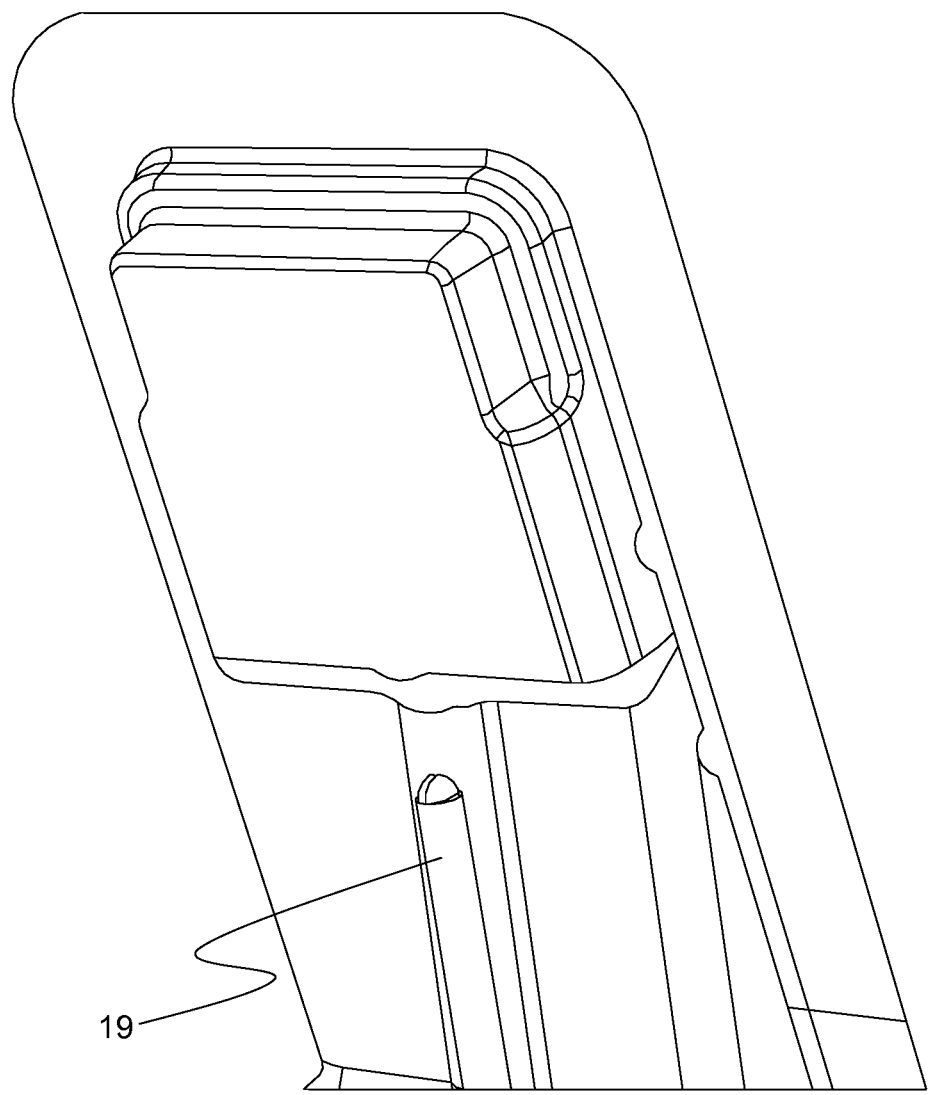

FIGS. 5A-5D illustrate different steps of removing an inserter from a package as illustrated in FIG. 4. In FIG. 5A, the handle 13 of the inserter is slightly raised from the container 9. FIGS. 5B to 5D show the packaged from the other side, and illustrate how the intrauterine system is withdrawn inside the insertion tube 19. Indeed, in FIG. 5B, it can be seen that the intrauterine system is already partially withdrawn inside the insertion tube 19, as the wings 20 of the system have partially folded towards one another. As can be seen from the Figure, the second part of the cover 18 is covering the container 9 at this end of the package. In FIG. 5C, the wings 20 almost touch each other as the IUS is further withdrawn inside the insertion tube 19. In FIG. 5D, the IUS is inside the insertion tube 19 (with only the tips of the wings protruding from the insertion tube) and the inserter is already partially removed from the package.

Figure 6:
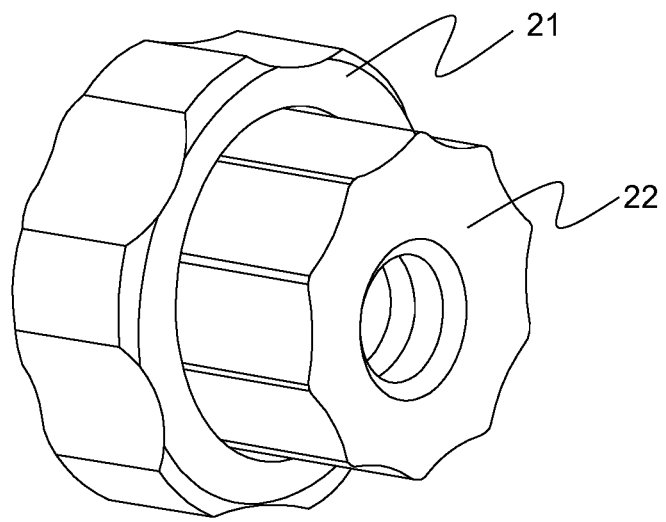
FIG. 6 illustrates a locking throttle according to an embodiment.

FIG. 6 illustrates a locking throttle according to an embodiment. In this embodiment, the locking throttle is designed to be turned by hand, during the packaging of the inserter. The locking throttle comprise two concentric parts, a larger part 21 and a smaller part 22, while the larger part 21 extends inside the smaller part 22, as can be seen in more detail below (in connection with a locking throttle according to another embodiment but with the same working principle).

Figure 7A:
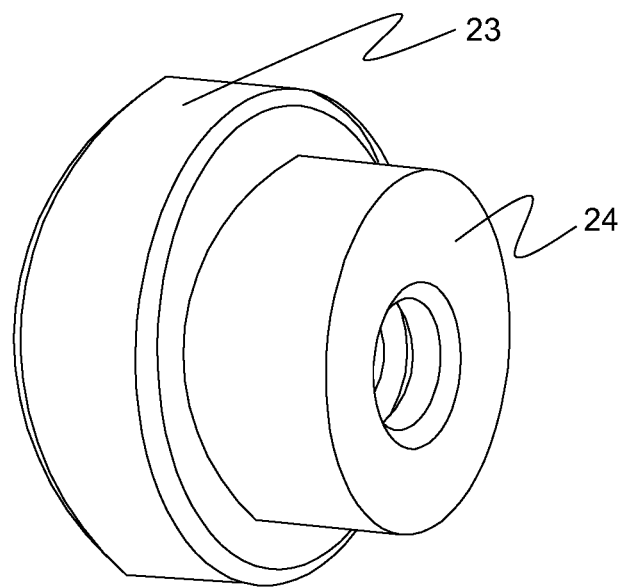
FIG. 7A-7D illustrate a locking throttle according to another embodiment.
Figure 7B:
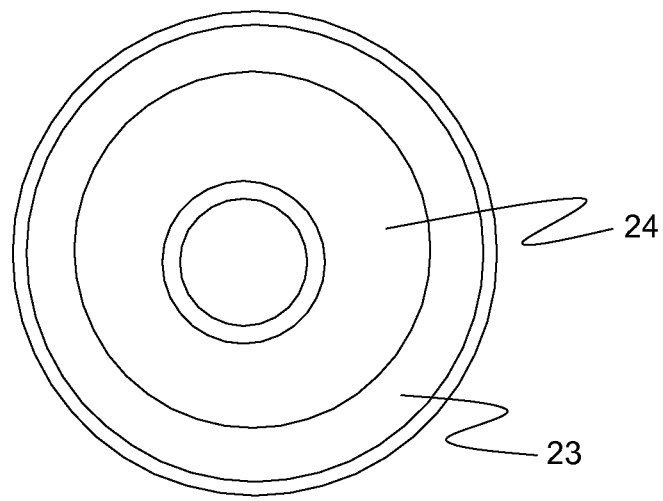
Figure 7C:
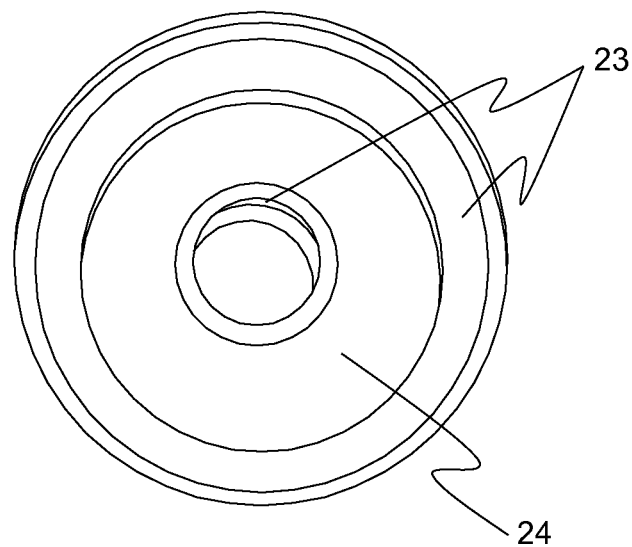
Figure 7D:
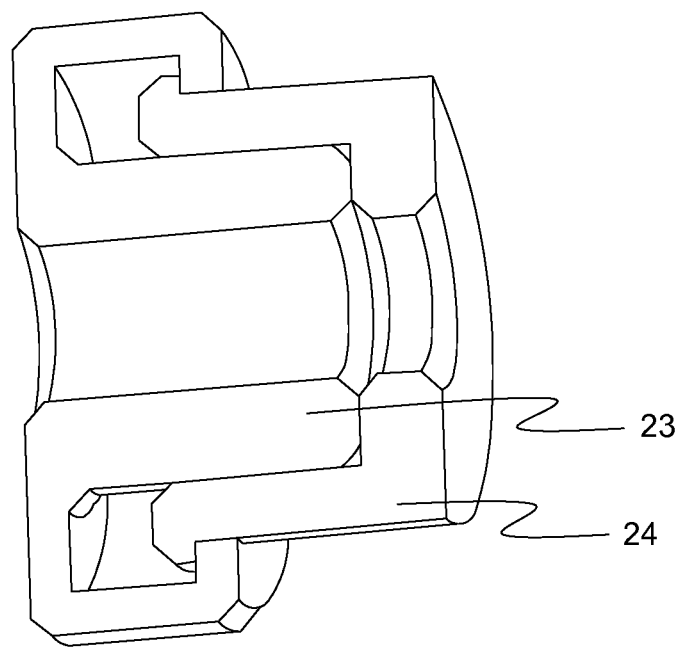

FIGS. 7A-7D illustrate a locking throttle according to another embodiment, for automatic handling. This locking throttle also comprises two parts, a larger part 23 and a smaller part 24. FIGS. 7B and 7C illustrate the locking throttle seen from its end, FIG. 7B in its open position (wherein the inside of the larger part 23 is not visible) and FIG. 7C in its closed position (wherein the inside of the larger part 23 can be seen in the opening). FIG. 7D shows a cross-section of the locking throttle, where it can be seen that the larger part 23 extends inside the smaller part 24.

Figure 8:
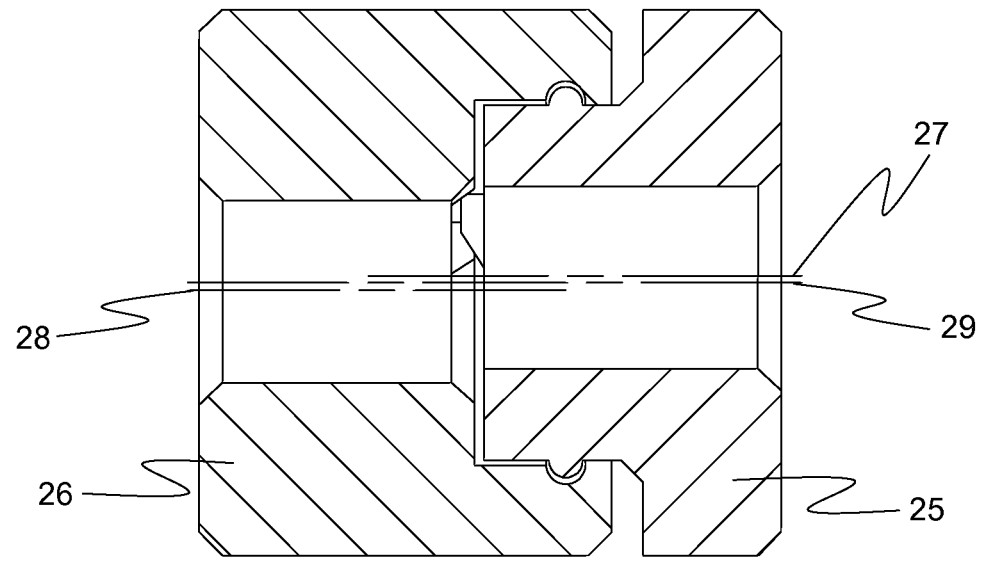
FIG. 8 illustrates a further embodiment of the locking throttle.

FIG. 8 illustrates a further embodiment of the locking throttle. The locking throttle is shown in a cross-sectional view, where a first part 25 is arranged partially inside a second part 26. As can be seen, the central axis 27 of the first part 25 is parallel to the central axis 28 of the second part 26, but the axes 27 and 28 are not aligned. The central axis 29 of the locking throttle is also illustrated, and located between the central axis of the two parts.

Figure 9A:
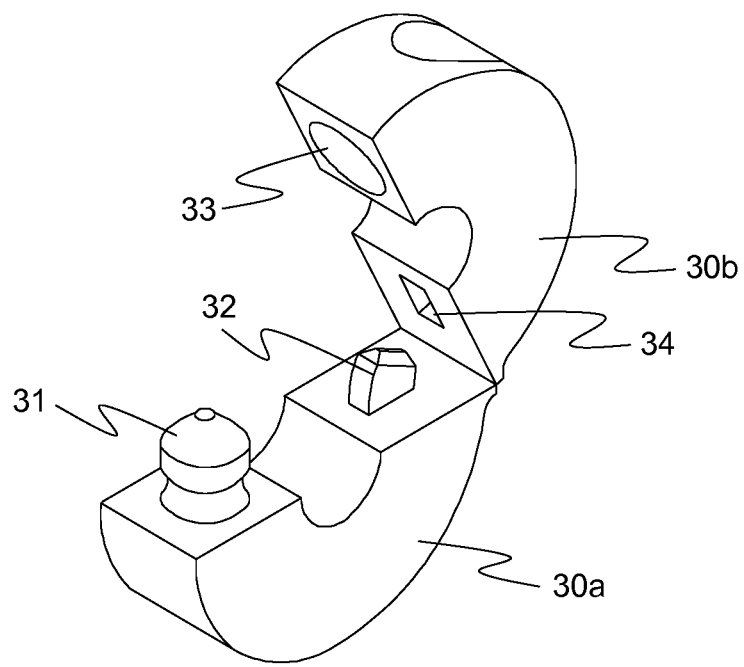
FIG. 9A-9C illustrate another embodiment of the locking throttle.
Figure 9B:
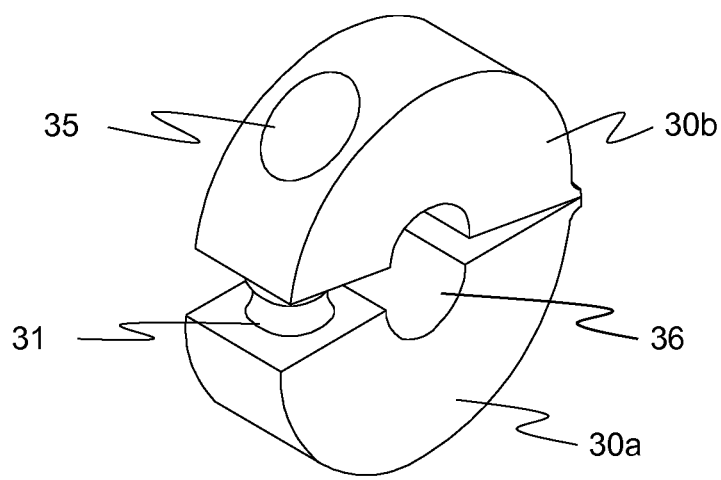
Figure 9C:
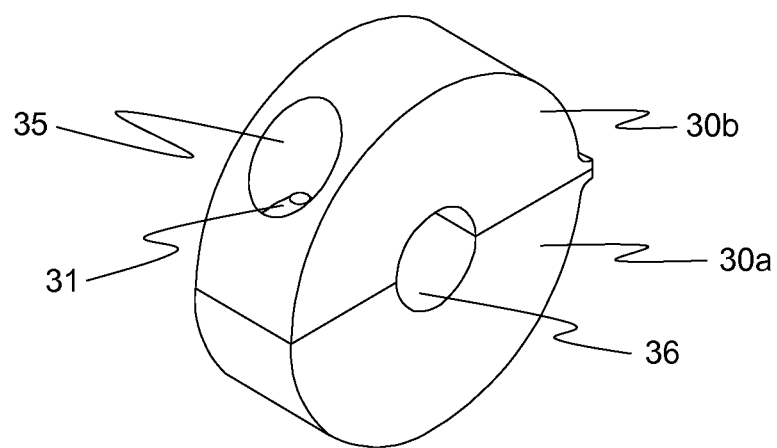

FIGS. 9A-9C illustrate another embodiment of the locking throttle. In this embodiment, the locking throttle comprises two parts 30a and 30b, which are attached to each other around a pivot line as seen in FIG. 9A, where the locking throttle is in an open position. One of the parts 30a comprises two protrusions 31 and 32, and the other part 30b comprises the corresponding openings 33 and 34. The protrusion 32 can be designed to guide the closing of the locking throttle and the protrusion 31, together with its opening 33 in the other part 30b of the locking throttle, can be designed to lock the locking throttle.

FIG. 9B shows the locking throttle almost closed, i.e. the parts 30a and 30b are almost in contact with each other. The tip of the protrusion 31 will be visible in the opening 35 (as is illustrated in FIG. 9C), and the parts 30a and 30b will define an opening 36 through the locking throttle.

The invention claimed is:

1. An intrauterine system arrangement comprising
   an intrauterine system;
   an inserter for the intrauterine system, the inserter comprising a handle having a first end and a second end with a longitudinal opening at said first end, an insertion tube having a first end and a second end; a first handling means for withdrawing the intrauterine system into the insertion tube, the first handling means comprising a movable slider arranged in said longitudinal opening and having a first end and a second end; a second handling means for expulsing the intrauterine system from the insertion tube, the second handling means comprising a plunger having a first end and a second end, said plunger attached by its second end to the handle; and locking means for reversibly locking the intrauterine system in relation to the plunger via a removal string; and
   a package for the inserter, the package comprising a container, a cover arranged to close the container, and a throttle configured to withdraw the intrauterine system into the insertion tube when the inserter is removed from the package.

2. The arrangement of claim 1, wherein the throttle comprises a form configured to exert a force of 10-30 N to the inserter when the inserter is pulled away from the container.

3. The arrangement of claim 1, wherein the throttle is a locking throttle arranged in connection with the container of the package.

4. The arrangement of claim 1, wherein the slider is configured to control the locking means.

5. The arrangement of claim 1, wherein the insertion tube is configured to control the locking means.

6. The arrangement of claim 1, wherein the cover is configured to open only partially.

7. The arrangement of claim 1, wherein the container comprises a plastic material.

8. The arrangement of claim 1, wherein the cover comprises a plastic material.

9. The arrangement of claim 8, wherein the cover comprises a fibre reinforced plastic material.

10. The arrangement of claim 1, wherein the intrauterine system comprises a T-shaped body and an elastomeric capsule comprising a therapeutically active agent.

11. The arrangement of claim 10, wherein the therapeutically active agent is a hormone.

12. A method for positioning an intrauterine system in the uterus of patient, comprising:
   providing the intrauterine system arrangement of claim 1,
   sounding the uterus of the patient to determine a depth of the uterus,
   opening the package,
   holding the handle of the inserter,
   pulling the inserter out of the package, during which pulling the intrauterine system is automatically loaded inside the insertion tube,
   setting a flange on the insertion tube according to the predetermined depth,
   introducing the inserter into the uterus of the patient until the intrauterine system is at the predetermined depth
   releasing the intrauterine system from the inserter by retracting the slider, which releases the removal string from the locking means, and
   removing the inserter from the uterus of the patient.

13. The method of claim 12, wherein the intrauterine system comprises a T-shaped body and an elastomeric capsule comprising a therapeutically active agent.

14. The method of claim 13, wherein the therapeutically active agent is a hormone.

15. A method of providing contraception to a patient in need thereof, comprising:
   providing the intrauterine system arrangement of claim 1,
   sounding the uterus of the patient to determine a depth of the uterus,
   opening the package,
   holding the handle of the inserter,
   pulling the inserter out of the package, during which pulling the intrauterine system is automatically loaded inside the insertion tube,
   setting a flange on the insertion tube according to the predetermined depth,
   introducing the inserter into the uterus of the patient until the intrauterine system is at the predetermined depth
   releasing the intrauterine system from the inserter by retracting the slider, which releases the removal string from the locking means, and
   removing the inserter from the uterus of the patient.

16. The method of claim 15, wherein the therapeutically active agent is a hormone.

* * * * *